United States Patent
Wang

(10) Patent No.: US 6,303,781 B1
(45) Date of Patent: Oct. 16, 2001

(54) METHOD FOR PREPARING MELAMINE

(75) Inventor: Yin Wang, Bellingham, WA (US)

(73) Assignee: DSM N.V. (NL)

( * ) Notice: Subject to any disclaimer, the term of this patent is extended or adjusted under 35 U.S.C. 154(b) by 0 days.

(21) Appl. No.: 09/709,550

(22) Filed: Nov. 13, 2000

Related U.S. Application Data

(63) Continuation of application No. PCT/NL99/00264, filed on May 3, 1999.
(60) Provisional application No. 60/085,065, filed on May 12, 1998.

(51) Int. Cl.$^7$ .................. C07D 251/60; C07D 251/62
(52) U.S. Cl. ........................... 544/201; 544/203
(58) Field of Search ..................... 544/201, 203

(56) References Cited

U.S. PATENT DOCUMENTS

| | | | |
|---|---|---|---|
| 3,116,294 | 12/1963 | Marullo et al. ............... | 544/201 |
| 3,308,123 | 3/1967 | Murata ........................... | 544/201 |
| 3,386,999 | 6/1968 | Manes ............................ | 544/201 |
| 5,514,796 | 5/1996 | Best et al. ..................... | 544/201 |
| 5,721,363 | * 2/1998 | Canzi et al. .................. | 544/201 |

FOREIGN PATENT DOCUMENTS 8105027   6/1983   (NL).

* cited by examiner

Primary Examiner—Mukund J. Shah
Assistant Examiner—Venkataraman Balasubramanian
(74) Attorney, Agent, or Firm—Pillsbury Winthrop LLP

(57) ABSTRACT

Method for preparing melamine from urea via a high-pressure process in which solid melamine is obtained by transferring the reactor product comprising liquid melamine, $CO_2$ and $NH_3$ to a gas/liquid separator and subsequently transferring the melamine melt coming from the separator to a vessel where the melamine melt is cooled with an evaporating cooling medium, characterized in that, the gas/liquid separation is conducted by addition of $5.10^{-4}$–$2.10^{-2}$ mole of water per mole of melamine.

4 Claims, No Drawings

METHOD FOR PREPARING MELAMINE

This application is a continuation of PCT/NL 99/00264 filed as May 3, 1999; which claims the benefit of U.S. Provisional Application No. 60/085,065, filed May 12, 1998.

The invention relates to a method for preparing melamine from urea via a high-pressure process in which solid melamine is obtained by transferring the reactor product comprising liquid melamine, $CO_2$ and $NH_3$ to a gas/liquid separator and subsequently transferring the melamine melt coming from the separator to a vessel where the melamine melt is cooled with a cooling medium.

Such a method is described, inter alia, in EP-A-747366. This describes a high-pressure process for preparing melamine from urea. In particular, EP-A-747366 describes how urea is pyrolysed in a reactor at a pressure of from 10.34 to 24.13 MPa and a temperature of from 354 to 454° C. to produce a reactor product. The reactor product obtained contains liquid melamine, $CO_2$ and $NH_3$ and is transferred under pressure as a mixed stream to a gas/liquid separator. In this gas/liquid separator, which is kept at virtually the same pressure and temperature as the said reactor, the said reactor product is separated into a gaseous stream and a liquid stream. The gaseous stream contains $CO_2$ and $NH_3$, waste gases and also melamine vapour. The liquid stream mainly comprises liquid melamine. The gaseous product is transferred to a scrubber unit, while the liquid melamine is transferred to a product-cooling unit. In the scrubber unit, the said $CO_2$ and $NH_3$ waste gases, which contain melamine vapour, are scrubbed with molten urea, at virtually the same pressure and temperature as the pressure and temperature of the reactor, to preheat the urea and to cool the said waste gases to a temperature of 177–232° C. and to remove the melamine present from the waste gases. Then the preheated molten urea, which contains the said melamine, is fed to the reactor. In the product-cooling unit, the liquid melamine is cooled with a liquid cooling medium, which forms a gas at the temperature of the liquid melamine in the product cooler, to produce a solid melamine product without scrubbing or further purification. In EP-A-747366 liquid ammonia is preferably used as the liquid cooling medium, the pressure in the product-cooling unit being above 4.14 MPa.

The purity of the melamine end product, according to EP-A-747366, is above 98.5 wt %, but it is not easy to achieve this level continuously on a constant level and on a commercial scale. This is a drawback, in particular when melamine is used in melamine-formaldehyde resins which are used in laminates and/or coatings. The impurities in the melamine end product, particularly when prepared on a commercial scale, consists primarily of melam, melem and oxygen containing impurities like ammelide, ammeline and urediomelamine.

The object of the present invention is to obtain an improved process for preparing melamine from urea, in which melamine is obtained as a dry powder having a high degree of purity. More in particular, the object of the present invention is to obtain an improved high-pressure process for preparing melamine from urea, in which melamine is obtained directly from the liquid melamine melt as a dry powder having a high degree of constant purity via cooling.

This object is achieved in that the gas/liquid separation is conducted by addition of $5.10^{-4}$–$2.10^{-2}$ mole of water per mole of melamine. The water added to the gas/liquid separator is preferably chosen to be lower than $10^{-2}$ mole per mole melamine and higher than $10^{-3}$ mole per mole melamine. This ratio is a ratio of the feed rates to the separator.

It has surprisingly been found that with the process according to the invention the amounts of oxygen-containing impurities in the melamine end product can be kept constant.

The advantage of the method according to the present invention is that a powdered melamine is obtained of a purity which is constant and above 98.5 wt %, which is sufficient for the melamine thus obtained to be used in virtually any melamine application. At the same time it is possible to obtain melamine powder having very good colour characteristics.

The use of water in order to prevent the formation of oxygen-containing impurities has never been distinguished in the prior art. U.S. Pat. No. 3,116,294 describes for example that, in order to obtain melamine with a purity higher than 99 wt %, raw melamine with a purity of 95% has to be heated in the presence of $NH_3$ alone explicitly in absence of water. It is therefor the more surprisingly that such good results are obtained with the process according to the invention in which the gas/liquid separation is performed in the presence of water. The water may be added to the gas/liquid separator, preferably via a pump.

The amount of water added to the gas/liquid separator in the process according to the invention is between $5.10^{-4}$ and $2.10^{-2}$ mole of water per mole of melamine. The water added to the gas/liquid separator is preferably chosen to be between $10^{-3}$ and $10^{-2}$ mole of water per mole of melamine. It is hypothesized that water reacts with isocyanic acid into ammonia an carbondioxide which will leave the melamine melt. So the amount of isocyanic acid in the melamine melt will be reduced by the reaction with water. The advantage is a less and constant ammelide content in the melamine which ammelide is believed to be produced from the isocyanic acid.

The preparation of melamine preferably starts from urea as the raw material in the form of a melt. $NH_3$ and $CO_2$ are by-products during the preparation of melamine, which proceeds according to the following reaction equation:

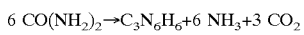
$$6\ CO(NH_2)_2 \rightarrow C_3N_6H_6 + 6\ NH_3 + 3\ CO_2$$

The preparation can be carried out at high pressure, preferably between 5 and 25 MPa, without the presence of a catalyst. The reaction temperature ranges between 325 and 450° C. and is preferably between 350 and 425° C. The by-products $NH_3$ and $CO_2$ are usually recycled to an adjoining urea plant.

The above-mentioned objective of the invention is achieved by employing an apparatus suitable for the preparation of melamine from urea. An apparatus suitable for the present invention may comprise a scrubber unit, a reactor, a gas/liquid separator, optionally a post-reactor and a cooling vessel.

In an embodiment of the invention, melamine is prepared from urea in an apparatus comprising a scrubber unit, a melamine reactor, a gas/liquid separator and a cooling vessel. Urea melt from a urea plant is fed to a scrubber unit at a pressure of from 5 to 25 MPa, preferably from 8 to 20 MPa, and at a temperature above the melting point of urea. This scrubber unit may be provided with a cooling jacket in order to ensure additional cooling within the scrubber. The scrubber unit may also be provided with internal cooling bodies. In the scrubber unit the liquid urea comes into contact with the reaction gases from the melamine reactor or from a separate gas/liquid separator downstream of the reactor. The pressure and temperature in the separate gas/liquid separator are virtually identical to the temperature and pressure in the melamine reactor. The reaction gases mainly consist of $CO_2$ and $NH_3$ and also comprise an amount of melamine vapour. The molten urea scrubs the melamine vapour from the waste gas and carries this melamine along back to the reactor. In the scrubbing process, the waste gases are cooled from the temperature of the reactor, i.e. from 350 to 425° C., to from 170 to 240° C., the urea being heated to from 170 to 240° C. The waste gases are removed from the top of the scrubber unit and, for example, recycled to a urea plant, where they are used as raw materials for the urea production.

The preheated urea is drawn off from the scrubber unit, together with the melamine scrubbed out, and supplied, for example via a high-pressure pump, to the reactor which has a pressure of from 5 to 25 MPa and preferably of from 8 to 20 MPa. Alternatively, the transfer of the urea melt to the melamine reactor may be effected by gravity, by the scrubber unit being positioned above the reactor.

In the reactor, the molten urea is heated to a temperature of from 325 to 450° C., preferably of from approximately 350 to 425° C., at a pressure as reported above, under which conditions the urea is converted into melamine, $CO_2$ and $NH_3$. A certain amount of ammonia can be metered into the reactor, for example in the form of a liquid or hot vapour. The ammonia supplied may serve, for example, to prevent the formation of condensation products of melamine such as melam, melem and melon, or to promote mixing in the reactor. The amount of ammonia supplied to the reactor is from 0 to 10 mol per mole of urea; preferably from 0 to 5 mol of ammonia is used and in particular from 0 to 2 mol of ammonia per mole of urea.

The $CO_2$ and $NH_3$ produced in the reaction as well as the additionally supplied ammonia collect in the separation section and are separated in the gaseous state from the liquid melamine.

To the gas/liquid separator downstream of the reactor is added $5.10^{-4}$–$2.10^{-2}$ mole of water per mole of melamine. The water added to the gas/liquid separator is preferably chosen to be lower than $10^{-2}$ mole per mole melamine and higher than $10^{-3}$ mole per mole melamine.

To the gas/liquid separator downstream of the reactor, it may be advantageous for ammonia to be metered into this separator. The amount of ammonia in this case is 0.01–10 mol of ammonia per mole of melamine, preferably 0.1–5 mol. This has the advantage that the carbon dioxide is rapidly separated off, thus preventing the formation of oxygen-containing impurities. It is preferred that ammonia and water are present in the gas/liquid separator in order to prevent the formation of oxygen-containing impurities and to avoid the formation of melem, melam and melon.

The gas mixture formed after gas/liquid separation is passed to the scrubber unit in order to remove melamine vapour and preheat the urea melt.

The liquid melamine having a temperature between the melting point of melamine and 450° C. is drawn off (from the reactor or) from the gas/liquid separator downstream of the reactor and, is rapidly cooled and depressurized using a liquid medium that is vapor at the conditions of the cooling unit, preferably ammonia.

What is claimed is:

1. Method for preparing melamine from urea via a high-pressure process in which solid melamine is obtained by transferring the reactor product comprising liquid melamine, $CO_2$ and $NH_3$ to a gas/liquid separator and subsequently transferring the melamine melt coming from the separator to a vessel where the melamine melt is cooled with an evaporating cooling medium, wherein, the gas/liquid separation is conducted by addition of $5.10^{-4}$–$2.10^{-2}$ mole of water per mole of melamine.

2. Method according to claim 1, wherein, $10^{-3}$–$10^{-2}$ mole of water per mole of melamine is added.

3. Method according to claim 1 wherein, the gas-liquid separation is conducted by addition of 0.01–10 mole of ammonia per mole of melamine.

4. Method according to claim 3, wherein, the gas-liquid separation is conducted by addition of 0.1–5 mole of ammonia per mole of melamine.

* * * * *